(12) United States Patent
Breton et al.

(10) Patent No.: US 6,586,020 B1
(45) Date of Patent: *Jul. 1, 2003

(54) BRADYKININ ANTAGONISTS COMPRISING ROSACEAE PLANT EXTRACTS

(75) Inventors: Lionel Breton, Versailles (FR); Nathalie Pineau, Poitiers (FR)

(73) Assignee: Societe L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/157,982

(22) Filed: Sep. 22, 1998

(30) Foreign Application Priority Data

Sep. 22, 1997 (FR) .......................................... 97 11762

(51) Int. Cl.[7] .............................................. A61K 35/78
(52) U.S. Cl. ...................................... 424/765; 424/725
(58) Field of Search ............................... 424/195.1, 765, 424/725; 514/880

(56) References Cited

U.S. PATENT DOCUMENTS

| | | | | |
|---|---|---|---|---|
| 4,855,131 A | * | 8/1989 | Iris | 424/74 |
| 5,407,675 A | * | 4/1995 | Etemad-Moghadam | 424/40 |

FOREIGN PATENT DOCUMENTS

| | | |
|---|---|---|
| EP | 0 332 382 | * 9/1989 |
| EP | 0727217 | 8/1996 |
| EP | 0781544 | 7/1997 |
| FR | 2719473 | 11/1995 |
| GB | 2095553 | 10/1982 |
| JP | 3-188014 | * 8/1991 |
| WO | 97/13493 | 4/1997 |

OTHER PUBLICATIONS

The Merck Manual of Diagnosis and Therapy 16th Edition, pp. 2433 and 2434, 1992.*
English abstract of Japanese Hei 6–65042 (1994).
English abstract of Japanese Hei 8–40922 (1996).
Nagamoto et al., "Active Components Having Anti–inflammatory and Analgesic Activites from Armeniacae Semen, Pruni Japonicae Semen and Almond Seeds", Shoyakugaku Zasshi 42(1), 81–88 (1988).
Arichi et al., "Studies on Persicae Semen. III. Oxygen Radical Scavenging Activity of PR–B, an Anti–inflammatory Protein of Persicae Semen", Yakugaku Zasshi 105(9), 895–901 (1985).
English abstract of Japanese Pubication 06065042 (1994).
JPAB, JP 403188014A, abstract of JP 03188014A, published Aug. 16, 1991.
Database WPI, Week 9139, Derwent Publications Ltd., London, GB; AN 91–284722 (1991).
Database WPI, Week 9139, Derwent Publications Ltd., London, GB; AN 91–284717 (1991).

* cited by examiner

*Primary Examiner*—Francisco Prats
(74) *Attorney, Agent, or Firm*—Burns, Doane, Swecker & Mathis, L.L.P.

(57) ABSTRACT

Disease states, disorders, conditions or afflictions manifesting excessive synthesis and/or release of bradykinin are therapeutically treating by administering to individuals in need of such treatment, an effective bradykinin antagonist amount of at least one extract of at least one plant of the Rosaceae family.

8 Claims, No Drawings

BRADYKININ ANTAGONISTS COMPRISING ROSACEAE PLANT EXTRACTS

CROSS-REFERENCE TO PRIORITY APPLICATION

This application claims priority under 35 U.S.C. §119 of FR-97/11762, filed Sep. 22, 1997, assigned to the assignee hereof and hereby expressly incorporated by reference.

CROSS-REFERENCE TO COMPANION APPLICATION

Our application Ser. No. 09/157,983 filed concurrently herewith and assigned to the assignee hereof.

BACKGROUND OF THE INVENTION

1. Technical Field of the Invention

The present invention relates to novel bradykinin antagonist compositions comprising at least one extract of at least one plant of the Rosaceae family.

This invention also relates to the administration of at least one plant of the Rosaceae family, as the active species or agent for treating disorders associated with an excessive synthesis and/or release of bradykinin.

2. Description of the Prior Art

Bradykinin is a peptide of plasma origin which is released from a kininogenic precursor by a plasma protease deemed kallikrein (EC 3.4.21.24). This nanopeptide is one of the key mediators of inflammation and exhibits mitogenic properties. The receptors for this kinin can be separated into two principal subtypes B1 and B2. Bradykinin acts especially on the B2 receptor and causes stimulation of numerous systems of production of second messengers, including inositol triphosphates (ip3), known to cause the release of calcium from the intracellular storage sites in the cells including the keratinocyte. Bradykinin also induces the phosphorylation of tyrosine residues through activation of the B2 receptor, depolarization or hyperpolarization of the cell membrane, as well as the activation of the metabolism of arachidonic acid.

Bradykinin is involved in a large number of physiopathological disorders such as, for example, vasodilation and increase in vascular permeability, hypotension, pain or the proliferation of the connective tissue. Vasodilation and increase in vascular permeability may have as consequence, inter alia, acne rosacea, telangiectasia or a rhynophyma. The proliferation of the connective tissue results in the formation of keloids.

Bradykinin is suspected of playing a role in the mechanism leading to hair loss.

Moreover, bradykinin causes an inflammatory response by activation of phospholipase A2 and by formation of prostaglandins and/or the release of various inflammation mediators, cytokines, leukotrienes. It is also involved in the stimulation of nerve endings, the contraction of the smooth muscles of the digestive and respiratory tracts and of the uterus. An excessive production of bradykinin may cause diarrhoeas in gastrointestinal disorders and stimulate the nasopharyngeal secretions in allergic rhinitis.

Bradykinin is moreover known to stimulate ion transport and fluid secretions by various epithelia.

The administration of bradykininergic antagonists is therefore one of the effective alternatives to all cosmetic and/or pathological disorders involving the systems described above, in particular inflammatory processes of neurogenic origin or otherwise.

For a substance to be recognized as a bradykinin antagonist, it should induce a coherent pharmacological response including or otherwise its attachment to the bradykinin receptor.

Thus, within this definition is any compound which may interfere with the effects of bradykinin by its attachment to the receptor for the latter (B1 or B2) and/or any compound which, independently of the attachment to the receptor(s), induces by any mechanism an effect which is the opposite of that known for bradykinin (for example, interfering with the synthesis of bradykinin).

In particular, for a substance to be recognized as a bradykinin receptor antagonist, it should, in particular, exhibit the following characteristics:

(a) have a selective affinity for the receptors specific for this compound: of the $B_1$ and/or $B_2$ type. The experimental models used are established on a culture of mesenteric aorta cells (receptor attachment to $B_1$ receptors according to the technique described by J. P. Galizzi published in *Brit. J. Pharmacol*, 113, 389 (1984)) and/or on the intestine (receptor attachment to $B_2$ receptors according to the technique described by Burch R. M. published in *Biotech. Update (Dupont-Nen)*, 7, 2 (1992); and/or (b) have a bradykinin receptor antagonist pharmacological activity, namely, induce a coherent pharmacological response in specific tests. The pharmacological activity is in this event evaluated on isolated organs according to the techniques described by Rhaleb N. E. et al., in *Brit. J. Pharmacol.*, 94, 445 (1990) as regards an antagonist activity of the $B_1$ and/or $B_2$ type.

Numerous compounds have already been recognized as bradykinin antagonists. Representative are the optionally modified synthetic or natural peptides such as D-Arg-[Hyp3, D-Phe7]-bradykinin (NPC567), [Thi 5, 8, D-Phe7]-bradykinin, D-Arg, [Hyp3, Thi5,8, D-Phe7]-bradykinin, N-α-adamantaneacetyl-D-Arg-[Hyp3, Thi5,8, D-Phe7]-bradykinin, des-Arg9, [Leu8]-bradykinin (all marketed by Sigma) or, alternatively, compounds described in WO-95/08566, WO-95/07294, EP-0623350, EP-0622361, WO-94/11021, EP-0596406, WO-94/06453, WO-94/09001, EP-0578521, EP-0564972, EP-0552106, WO-93/11789, U.S. Pat. No. 5,216,165, U.S. Pat. No. 5,212,182, WO-92/17201, EP-0496369, EP-0472220, EP-0455133, WO-91/09055, WO-91/02746, EP-0413277, EP-0370453, EP-0359310, WO-90/03980, WO-89/09231, WO-89/09230, WO-89/01780, EP-0334244, EP-0596406, WO-86/07263 or P-guanido-benzoyl-[Hyp3,Thi5,D-Tic7,Oic8]-bradykinin (S 16118) (Feletou M & al., *Pharmacol. Exp. Ther.*, June 1995, 273, 1078–84), D-Arg-[Hyp3, Thi5, D-Tic7,Oic8]-bradykinin (HOE 140) (Feletou M & al., *Eur. J. Pharmacol*, 1995, 274, 57–64), D-Arg-[Hyp3, D-Hype (trans-propyl)7 Oic8]-bradykinin (NPC 17731) (Herzig M. C. S. and Leeb-Lundberg L. M. F., *J. Biol. Chem.*, 1995, 270, 20591–20598) or those indicated in *Bradykinin Antagonists: development and applications* (Stewart J. M., *Biopolymers*, 1995, 37, 143–155), or, alternatively, synthetic or natural chemical molecules such as, for example, those described in Salvino et al., *J. Med. Chem.*, 3, 2583–2584 (1993).

As a general rule, these bradykinin antagonists which, moreover, provide excellent results, are chemical molecules which may have harmful side effects.

Serious need continues to exist for novel active agents or species which meet the criteria for a bradykinin antagonist, especially if they are of natural origin and are devoid of side effects.

Heretofore, it has never been demonstrated or suggested in the prior art that an extract of at least one plant of the Rosaceae family exhibits the criteria for a bradykinin antagonist.

Indeed, plants of the Rosaceae family are principally used for their aromatic and ornamental properties.

In the prior art, plants of the Rosaceae family have been included in compositions for the treatment of urogenital diseases (FR-76/36295), in lightening cosmetic compositions (JP-08208451) or in compositions for protecting against ultraviolet radiation (EP-A-781544), for the preparation of antioxidant compounds (EP-A-94/401669), or, alternatively, for the preparation of antimicrobial and/or insecticidal compounds for the protection of plants (DE-4327792).

SUMMARY OF THE INVENTION

It has now unexpectedly and surprisingly been determined that extracts of at least one plant of the Rosaceae family elicit bradykinin-antagonizing activity.

Thus, it has now been determined that an extract of at least one plant of the Rosaceae family presents the characteristics defined as characterizing a bradykinin antagonist and can therefore be administered as a bradykinin antagonist.

Accordingly, the present invention features cosmetic/pharmaceutical compositions comprising an effective active agent amount of at least one Rosaceae extract which serves as a bradykinin antagonist.

DETAILED DESCRIPTION OF BEST MODE AND SPECIFIC/PREFERRED EMBODIMENTS OF THE INVENTION

More particularly according to the present invention, by "active ingredient" is intended any molecule or extract capable of modifying or of modulating the functioning of at least one given biological system.

The extract of at least one plant of the Rosaceae family may be any extract prepared from any plant material derived from at least one plant of the Rosaceae family.

Thus, the extract of at least one plant of the Rosaceae family according to the invention may be obtained from plant material derived from a whole plant, or from a plant portion such as the leaves, stems, flowers, petals, roots or from undifferentiated cells.

By "undifferentiated plant cell" is intended any plant cell exhibiting none of the characteristics of a specific specialization and capable of living or remaining viable by itself and not in dependence on other cells. These undifferentiated plant cells may be capable, under the influence of an induction, of any differentiation consistent with their genome.

According to the technique of culture selected, and in particular according to the selected culture medium, it is possible to obtain, from the same explant, undifferentiated plant cells having different characteristics.

Preferably according to the invention, petals are employed.

The extract of at least one plant of the Rosaceae family may be any extract prepared from any plant material derived from at least one plant of the Rosaceae family cultured in vivo or derived from in vitro culture.

By "in vivo culture" is intended any culture of a conventional type, namely, in the soil, outdoors or in a greenhouse, or, alternatively, soil-free culture.

By "in vitro culture" is intended the range of techniques known to this art which makes it possible to artificially obtain a plant or a portion of a plant. The selection pressure imposed by the physicochemical conditions during the growth of plant cells in vitro makes it possible to obtain a plant material which is standardized and available throughout the year, contrary to the plants cultured in vivo.

Preferably according to the invention, a plant derived from in vivo culture is employed.

Any extraction technique known to this art may be used to prepare the extract contained in the compositions according to the invention.

Exemplary are those utilizing, in particular, aqueous or alcoholic extracts, or extracts obtained from an organic solvent.

By "aqueous solvent" is intended any solvent consisting completely or partly of water. Exemplary are water itself, aqueous/alcoholic solvents in any proportion or, alternatively, solvents comprising water and a compound such as propylene glycol in any proportion.

Among the alcoholic solvents, ethanol is particularly representative.

An extract prepared by the method described in French patent application No. 95-02379, assigned to the assignee hereof, is also exemplary.

Thus, in a first step, the plant material is ground in an aqueous solution at cold temperature, in a second step, the particles in suspension are removed from the aqueous solution derived from the first step, and, in a third step, the aqueous solution derived from the second step is sterilized. This aqueous solution corresponds to the extract.

Moreover, the first step may advantageously be replaced by a simple operation of freezing the plant tissues (for example at −20° C.), followed by an aqueous extraction comprising the second and third steps described above.

Regardless of the mode of preparation according to the invention, subsequent steps intended to promote preservation and/or stabilization may be included without as a result modifying the actual nature of the extract. Thus, for example, the extract obtained may be freeze-dried by any conventional freeze-drying method. A powder is thus obtained which may be used directly or, alternatively, mixed in an appropriate solvent before use.

Preferably, according to the invention, an aqueous extract and even more preferably an extract prepared with a solvent composed of water and of propylene glycol marketed under the trademark Herbasol® by Cosmetochem, is used.

The Rosaceae family comprises 27 genera including, for example, the genera Agrimonia, Amygdalus, Armeniaca, Cerasus, Malus, Mespilus, Persica, Pirus, Prunus, Rosa, Rubus.

Thus, the Rosaceae extract of the invention is an extract prepared from material derived from at least one plant belonging to a genus selected from among Agrimonia, Amygdalus, Armeniaca, Cerasus, Malus, Mespilus, Persica, Pirus, Prunus, Rosa, Rubus.

Preferably, the plant belongs to the Rosa genus.

The Rosa genus comprises more than 1,000 species including, for example, *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa* or *Rosa villosa*.

Thus, the plant extract of the Rosa genus of the invention is an extract prepared from material derived from at least one plant belonging to a species selected from among *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa, Rosa villosa*.

Preferably, the plant belongs to the species *Rosa gallica*.

Exemplary disorders associated with an excessive synthesis and/or release of bradykinin were set forth in the above text.

The present invention thus features, as active ingredient, in a cosmetic/pharmaceutical composition, an effective amount of at least one extract of a plant of the Rosaceae family, the extract or the composition being well suited for treating physiopathological disorders associated with an excessive synthesis and/or release of bradykinin.

Thus, in one specific embodiment of the invention, an effective amount of at least one extract of a plant of the Rosaceae family is formulated into a cosmetic/pharmaceutical composition, the extract (i.e., the active agent/species) or the composition being well suited for treating vasodilation and increase in vascular permeability, hypotension, pain, proliferation of the connective tissue, inflammation, hair loss, diarrhoeas, allergic rhinitis, the contraction of the smooth muscles of the digestive and respiratory tracts and of the uterus.

The present invention more particularly features compositions comprising an effective amount of at least one extract of a plant of the Rosaceae family, the extract or the composition being useful for treating acne rosacea, telangiectasia, a rhynophyma or for preventing the formation of keloids.

Regardless of the form of the composition according to the invention, the amount of Rosaceae extract therein of course depends on the desired effect and can therefore vary widely.

To provide an order of magnitude, in the compositions according to the invention the extract of at least one plant of the Rosaceae family is advantageously present in an amount representing from 0.01% to 30% of the total weight of the composition and, preferably, in an amount representing from 0.1% to 20% of the total weight of the composition.

The compositions according to the invention may be for cosmetic or pharmaceutical use.

Regardless of the form of the composition according to the invention in which at least one Rosaceae extract is formulated, it may be ingested, injected or topically applied to the skin (over any skin region of the body), the hair, the nails or the mucous membranes (buccal, jugal, gingival, genital, conjunctiva). Depending on the mode of administration, the composition according to the invention may be provided in any of the galenic forms conventional to this art.

For topical application onto the skin, the composition may especially be in the form of an aqueous or oily solution or of a dispersion of the lotion or serum type, of emulsions of liquid or semiliquid consistency of the milk type, which are obtained by dispersing a fatty phase in an aqueous phase (O/W) or conversely (W/O), or of suspensions or emulsions of soft consistency of the aqueous or anhydrous cream or gel type, or, alternatively, of microcapsules or microparticles, or of vesicular dispersions of the ionic and/or nonionic type. These compositions are formulated according to the customary techniques.

The subject compositions may also be used for the hair in the form of aqueous, alcoholic or aqueous\alcoholic solutions, or in the form of creams, gels, emulsions, lotions, foams or in the form of aerosol compositions also comprising a pressurized propelling agent.

For injection, the composition may be provided in the form of an aqueous or oily lotion or in the form of a serum.

For the eyes, it may be provided in the form of drops, and for ingestion, it may be provided in the form of capsules, granules, syrups or tablets.

The amounts of the various constituents of the compositions according to the invention are those that are conventional in the fields under consideration.

These compositions are advantageously creams for cleansing, protecting, treating or caring for the face, for the hands, for the feet, for the large anatomical skin-folds or for the body, (for example day creams, night creams, makeup removing creams, foundation creams, antisun or sunscreen creams), fluid foundations, makeup removing milks, body protecting or care milks, antisun or sunscreen milks, skincare lotions, gels or foams, such as cleansing lotions, antisun or sunscreen lotions, artificial tanning lotions, bath compositions, deodorant compositions comprising a bactericidal agent, aftershave gels or lotions, depilatory creams, compositions for combating insect bites, analgesic compositions, compositions for treating certain skin diseases such as eczema, rosacea, psoriasis, lichens, severe pruritus, etc.

The compositions according to the invention may also be formulated as solid preparations constituting cleansing cakes or soaps.

The compositions may also be packaged in the form of an aerosol composition, also comprising a pressurized propelling agent.

The compositions according to the invention may also be compositions for hair care, and especially a shampoo, a hair setting lotion, a treatment lotion, a hair styling gel or cream, a dyeing composition (especially oxidation dyes) optionally in the form of coloring shampoos, restructuring lotions for the hair, a permanent-waving composition (especially a composition for the first stage of a permanent waving), a lotion or gel for preventing hair loss, an antiparasitic shampoo and the like.

The subject compositions may also be for dentibuccal use, for example a toothpaste. In this event, the composition may contain customary adjuvants and additives for buccal use and especially surfactants, thickeners, humectants, polishing agents such as silica, various active ingredients such as fluorides, in particular sodium fluoride, and optionally sweeteners such as sodium saccharinate.

When the composition is an emulsion, the proportion of the fatty phase advantageously ranges from 5% to 80% by weight, and preferably from 5% to 50% by weight relative to the total weight of the composition. The oils, waxes, emulsifiers and coemulsifiers included in the composition in the form of an emulsion are selected from among those conventional in the cosmetic field. The emulsifier and coemulsifier are advantageously present in the composition in a proportion ranging from 0.3% to 30% by weight, and preferably from 0.5% to 20% by weight relative to the total weight of the composition. The emulsion may, in addition, contain lipid vesicles.

When the composition is an oily gel or solution, the fatty phase may represent more than 90% of the total weight of the composition.

In known fashion, the cosmetic composition may also contain usual adjuvants and additives in the cosmetic field, such as hydrophilic or lipophilic gelling agents, hydrophilic or lipophilic additives, preservatives, antioxidants, solvents, perfumes, fillers, screening agents, odor absorbers and colorants. The amounts of these various adjuvants and additives are those conventional in the cosmetic field, and advantageously range from 0.01% to 10% of the total weight of the composition. These adjuvants and additives, depending on their particular nature, may be introduced into the fatty phase, into the aqueous phase and/or into the lipid spherules.

Exemplary oils or waxes according to the invention include mineral oils (petroleum jelly), vegetable oils (liquid fraction of shea butter, sunflower oil), animal oils (perhydrosqualene), synthetic oils (Purcellin oil), silicone oils or waxes (cyclomethicone) and fluorinated oils (perfluoropolyethers), beeswax, carnauba wax or paraffin. Fatty alcohols and fatty acids (stearic acid) may be added to these oils.

Exemplary emulsifiers according to the invention include glycerol stearate, polysorbate 60 and PEG-6/PEG-32/Glycol Stearate mixture marketed under the trademark Tefose® 63 by Gattefosse.

Exemplary solvents include the lower alcohols, especially ethanol and isopropanol, propylene glycol.

And exemplary hydrophilic gelling agents according to this invention include carboxyvinyl polymers (carbomer), acrylic copolymers such as acrylate/alkylacrylate copolymers, polyacrylamides, polysaccharides such as hydroxypropyl cellulose, naturally occurring gums and clays, and, exemplary lipophilic gelling agents include modified clays such as bentones, metal salts of fatty acids such as aluminum stearates and hydrophobic silica, ethyl cellulose, polyethylene.

The subject compositions may contain other hydrophilic active agents such as proteins or protein hydrolysates, amino acids, polyols, urea, allantoin, sugars and sugar derivatives, water-soluble vitamins, plant extracts and hydroxy acids.

Representative lipophilic active agents include retinol (vitamin A) and derivatives thereof, tocopherol (vitamin E) and derivatives thereof, essential fatty acids, ceramides, essential oils, salicylic acid and derivatives thereof.

According to this invention, the composition may include at least one Rosaceae extract formulated in combination with other active agents intended, especially, for the prevention and/or treatment of a variety of skin conditions. Exemplary such active agents are:

(a) agents modulating skin pigmentation and/or proliferation and/or differentiation, such as retinoic acid and isomers thereof, retinol and esters thereof, vitamin D and derivatives thereof, estrogens such as estradiol, kojic acid or hydroquinone;

(b) antibacterial agents such as clindamycin phosphate, erythromycin or antibiotics of the class of tetracyclines;

(c) antiparasitic agents, in particular metronidazole, crotamiton or pyrethrinoids;

(d) antifungal agents, in particular the compounds belonging to the class of imidazoles such as econazole, ketoconazole or miconazole or their salts, polyene compounds, such as amphotericin B, compounds of the family of allylamines, such as terbinafin, or alternatively octopirox;

(e) antiviral agents such as acyclovir;

(f) steroidal anti-inflammatory agents, such as hydrocortisone, betamethasone valerate, clobetasol propionate, or nonsteroidal anti-inflammatory agents such as ibuprofen and its salts, diclofenac and its salts, acetylsalicylic acid, acetaminophen or glycyrrhetinic acid;

(g) anaesthetic agents such as lidocaine hydrochloride and derivatives thereof;

(h) antipruriginous agents such as thenaldine, trimeprazine or cyproheptadine;

(i) keratolytic agents such as alpha- and beta-hydroxycarboxylic or beta-ketocarboxylic acids, their salts, amides or esters and more particularly hydroxy acids such as glycolic acid, lactic acid, salicylic acid, citric acid and in general fruit acids, and 5-n-octanoylsalicylic acid;

(j) anti-free radical agents, such as alpha-tocopherol or its esters, superoxide dismutases, certain metal chelators or ascorbic acid and its esters;

(k) antiseborrhoeic agents such as progesterone;

(l) antidandruff agents such as octopirox or zinc pyrithione;

(m) antiacne agents such as retinoic acid or benzoyl peroxide;

(n) plant extracts or extracts of microbial origin.

The present invention also features a cosmetic regime or regimen for reducing the irritant effect of a normally irritating substrate (e.g., active agent or composition), comprising topically applying a cosmetic composition containing at least one Rosaceae extract as described above onto the skin, the hair and/or the mucous membranes.

The cosmetic treatment of the invention comprises administering the hygiene or cosmetic compositions as described above according to the usual technique for such compositions. For example: application of creams, gels, sera, lotions, makeup removing milks or antisun (sunscreen) compositions to the skin or to dry hair, application of a hair lotion to wet hair, of shampoos, or application of dentifrice to the gums.

In order to further illustrate the present invention and the advantages thereof, the following specific examples are given, it being understood that same are intended only as illustrative and in nowise limitative.

In said examples to follow, all parts and percentages are given by weight, unless indicated otherwise.

EXAMPLE 1

Bioloaical Activity of a Rosa Gallica Extract:

The extract used in the tests presented here was a *Rosa gallica* extract marketed under the trademark Herbasol® by Cosmetochem.

(1) Measurement of the receptor affinity:

The measurement of the receptor affinity of the extract for the bradykinin $B_2$ receptor was carried out according to the technique described by Jong, Y. J. L. et al., PNAS-USA, 90, 10994 (1993).

During each study, the reference molecule for the receptor studied (NPC567) was tested at eight (8) concentrations (n=2) in order to obtain a standard curve permitting the experiment to be validated.

There were thus obtained:

30% attachment for the extract at 1%

74% attachment for the extract at 5%

84% attachment for the extract at 10%.

The results of this experiment demonstrated affinity of the *Rosa gallica* extract for the human bradykinin $B_2$ receptor at concentrations of less than 1%.

The $IC_{50}$ value was close to 1%.

(2) Measurement of the bradykinin-antagonizing activity:

A functional test ex vivo carried out on the type $B_2$ bradykinin receptors present on the jugular vein isolated from rabbits was carried out in order to demonstrate the type $B_2$ bradykinin-antagonizing character.

The ex vivo experiments were carried out according to the Rhaleb, N. E. et al. technique described in *Brit. J. Pharmacol.*, 99, 445 (1990).

After establishment in experimental tanks, the tissues (smooth muscles) were subjected to an initial tension of 1 g. An equilibration period of at least 60 minutes, during which the physiological solution was replaced several times and the initial tension readjusted, was then observed before adding the extract.

The experiments were performed in the continuous presence of atropine ($3\times10^{-6}$ M) of pyrilamine ($3\times10^{-6}$ M) and of indomethacin ($10^{-6}$ M) in order to eliminate the indirect effects of mediators used during the stimulation of other types of receptor present on this tissue.

Each preparation was initially stimulated by a B2 agonist at the concentration of $3\times10^{-9}$ M which induced contractions. A $B_2$ specific antagonist then simply had to be placed in the medium to observe the disappearance of these contractions in a dose-dependent manner.

There were thus obtained:

48% attachment for the extract of Example 1 at 0.5%

79% attachment for the extract of Example 1 at 1%

97% attachment for the extract of Example 1 at 5%

These results evidenced that the Rosaceae extract had a bradykinin-antagonizing activity. This activity was preferably expressed on the B2 receptor.

EXAMPLE 2

Specific examples of formulations according to the invention are set forth below, particularly compositions including at least one extract of Rosaceae petals together with an active species eliciting an irritant effect on the skin, hair or mucous membranes.

These compositions were formulated simply by intimately admixing various components.

| Composition 1: Lotion | |
|---|---|
| Herbasol ® | 1.00 |
| Antioxidant | 0.05 |
| Isopropanol | 40.00 |
| Preservative | 0.30 |
| Water | qs 100% |
| Composition 2: Care gel | |
| Herbasol ® | 4.00 |
| Hydroxypropyl cellulose* | 1.00 |
| Antioxidant | 0.05 |
| Isopropanol | 40.00 |
| Preservative | 0.30 |
| Water | qs 100% |
| Composition 3: Care cream (oil-in-water emulsion) | |
| Herbasol ® | 5.00 |
| Glycerol stearate | 2.00 |
| Polysorbate 60** | 1.00 |
| Stearic acid | 1.40 |
| Triethanolamine | 0.70 |
| Carbomer | 0.40 |
| Liquid fraction of shea butter | 12.00 |
| Perhydrosqualene | 12.00 |
| Antioxidant | 0.05 |
| Perfume | 0.50 |
| Preservative | 0.30 |
| Water | qs 100% |
| Composition 4: Shampoo | |
| Herbasol ® | 2.00 |
| Hydroxypropyl cellulose* | 1.00 |
| Perfume | 0.50 |
| Preservative | 0.30 |
| Water | qs 100% |
| Composition 5: Care cream (oil/water emulsion) | |
| Herbasol ® | 4.00 |
| Glycerol stearate | 2.00 |
| Polysorbate 60** | 1.00 |
| Stearic acid | 1.40 |
| 5-n-Octanoylsalicylic acid | 0.50 |
| Triethanolamine | 0.70 |
| Carbomer | 0.40 |
| Liquid fraction of shea butter | 12.00 |
| Perhydrosqualene | 12.00 |
| Antioxidant | 0.05 |
| Perfume | 0.50 |
| Preservative | 0.30 |
| Water | qs 100% |
| Composition 6: Analgesic gel | |
| Herbasol ® | 10.00 |
| Hydroxypropyl cellulose* | 1.00 |
| Antioxidant | 0.05 |
| Lidocaine hydrochloride | 2.00 |
| Isopropanol | 40.00 |
| Preservative | 0.30 |
| Water | qs 100% |
| Composition 7: Solar erythema care cream (oil-in-water emulsion) | |
| Herbasol ® | 2.00 |
| Glycerol stearate | 2.00 |
| Polysorbate 60** | 1.00 |
| Stearic acid | 1.40 |
| Glycyrrhetinic acid | 2.00 |
| Triethanolamine | 0.70 |
| Carbomer | 0.40 |
| Liquid fraction of shea butter | 12.00 |
| Sunflower oil | 10.00 |
| Antioxidant | 0.05 |
| Perfume | 0.50 |
| Preservative | 0.30 |
| Water | qs 100% |
| Composition 8: Gel for the treatment of acne | |
| Herbasol ® | 8.00 |
| All-trans-retinoic acid | 0.05 |
| Hydroxypropyl cellulose* | 1.00 |
| Antioxidant | 0.05 |
| Isopropanol | 40.00 |
| Preservative | 0.30 |
| Water | qs 100% |
| Composition 9: Lotion for removing scars due to acne | |
| Herbasol ® | 8.00 |
| Glycolic acid | 50.00 |
| Hydroxypropyl cellulose* | 0.05 |
| NaOH | qs pH = 2.8 |
| Ethanol | qs 100% |
| Preservative | 0.30 |

*Klucel H ® marketed by Hercules
**Tween 60 ® marketed by ICI

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method or regimen for therapeutically treating hair loss accompanying abnormally increased synthesis and/or release of bradykinin, consisting essentially of administering to an individual subject in need of such treatment, an effective bradykinin antagonist amount of at least one extract of at least one plant of the Rosaceae family, said extract(s) being the only active ingredient(s) effective in treating hair loss, wherein said plant of the Rosaceae family is selected from the group consisting of at least one of the species *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa* and *Rosa villosa*, with the proviso that said extract is not used in combination with a mixture of 41–51 parts by wt. of glycerine, 38–48 parts by wt. of rosewater, 3–5 parts by wt. of liquid paraffin and 2–4 parts by wt. of olive oil.

2. The method or regimen as defined by claim 1, said at least one extract of at least one plant of the Rosaceae family having been derived from a whole plant, or from the leaves, stems, flowers, petals, root or undifferentiated cells thereof.

3. The method or regimen as defined by claim 2, said at least one extract of at least one plant of the Rosaceae family having been derived from the petals thereof.

4. The method or regimen as defined by claim 2, said at least one extract being obtained from at least one plant of the Rosaceae family that has been cultured in vivo.

5. The method or regimen as defined by claim 1, said at least one species comprising *Rosa gallica*.

6. A method or regimen for therapeutically treating hair loss accompanying abnormally increased synthesis and/or release of bradykinin, comprising administering to an individual subject in need of such treatment, a cosmetic/pharmaceutical composition consisting essentially of an effective bradykinin antagonist amount of at least one extract of at least one plant of the Rosaceae family, said extract(s) being the only active ingredient(s) in said composition effective in treating hair loss, wherein said plant of the Rosaceae family is selected from the group consisting of at least one of the species *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa* and *Rosa villosa*.

7. The method or regiment as defined by claim 6, said at least one species comprising *Rosa gallica*.

8. The method or regimen as defined by claim 6, said extract present in the composition in an amount ranging from 0.01% to 30% of the total weight of the composition.

* * * * *